United States Patent [19]

Nishida et al.

[11] Patent Number: 5,420,008

[45] Date of Patent: May 30, 1995

[54] ASSAY METHOD AND ASSAY REAGENT FOR SERUM IRON OR UNSATURATED IRON BINDING CAPACITY

[75] Inventors: Hozumi Nishida, Osaka; Masatsugu Nonobe, Hyogo; Tsuyoshi Fujita, Osaka, all of Japan

[73] Assignee: Oriental Yeast Co., Ltd., Tokyo, Japan

[21] Appl. No.: 94,188

[22] PCT Filed: Nov. 30, 1992

[86] PCT No.: PCT/JP92/01566

§ 371 Date: Aug. 2, 1993

§ 102(e) Date: Aug. 2, 1993

[87] PCT Pub. No.: WO93/11259

PCT Pub. Date: Oct. 6, 1993

[30] Foreign Application Priority Data

Dec. 2, 1991 [JP] Japan ................... 3-341808
Jun. 9, 1992 [JP] Japan ................... 4-173730
Jun. 19, 1992 [JP] Japan ................... 4-184634

[51] Int. Cl.⁶ ................... C12Q 1/527; C12Q 1/00; C12Q 1/32; C12N 9/88
[52] U.S. Cl. ................... 435/4; 435/18; 435/26; 435/183; 435/189; 435/190; 435/195; 435/232; 436/74; 436/84; 436/910
[58] Field of Search ................... 435/4, 18, 26, 183, 435/189, 190, 195, 232; 436/74, 84, 910

[56] References Cited

U.S. PATENT DOCUMENTS

| | | | |
|---|---|---|---|
| 3,537,822 | 11/1970 | O'Malley et al. | 436/74 |
| 4,308,027 | 12/1981 | Ceriotti | 436/74 |
| 4,588,695 | 5/1986 | Takano et al. | 436/87 |
| 4,657,854 | 4/1987 | Wegfahrt, Jr. | 435/14 |
| 5,151,370 | 9/1992 | Denney | 436/74 |

FOREIGN PATENT DOCUMENTS

| | | |
|---|---|---|
| 0286039 | 12/1987 | European Pat. Off. |
| 0529160 | 3/1977 | Japan |
| 60-69557 | 4/1985 | Japan |
| 2156160 | 6/1990 | Japan |
| 2167476 | 6/1990 | Japan |

OTHER PUBLICATIONS

Lowenstein, "Citric Acid Cycle", Methods in Enzymology, vol. 13, 446–450, 1969.
Rouault, T. A., et al., *Structural Relationships between an Iron-regulated RNA-Binding Protein(IRE-BP) and Acontiase: Functional Implications*, CELL, vol. 64, Mar. 8, 1992, pp. 881–883.
Villafranco et al., *The Mechanism of Aconitase Action*, The Journal of Biological Chemistry, vol. 246, Feb. 10, 1971, pp. 772–779.
Rose et al., *Mechanism of Aconitase Action*, The Journal of Biological Chemistry, vol. 242, Apr. 25, 1967, pp. 1870–1879.
Rose et al., *Intramolecular Hydrogen Transfer in the Phosphoglucose Isomerase Reaction*, Journal of Biological Chemistry, vol. 236, Dec. 1961, pp. 3086–3092.
Digest, *Properties as Iron-Sulfur Protein*, Proteins, Nucleic Acids and Enzymes, vol. 22, 1977, pp. 1293–1302.
Masui, Hideo, *Increase in Activity of NADH Oxidase System and Development of Mitochondrial Structure by Recovery from Iron-Deficieny in Saccharomyces cerevisiae*, Journal of Science of the Hiroshima University, vol. 23, 1991, pp. 369–376.
Villafranca et al., *The Mechanism of Aconitase Action*, The Journal of Biological Chemistry, vol. 246, No. 3, pp. 772–779, 10 Feb. 1971.

Primary Examiner—Michael G. Wityshyn
Assistant Examiner—Nancy J. Gromet
Attorney, Agent, or Firm—Browdy and Neimark

[57] ABSTRACT

The present invention measures serum iron by liberating iron from transferrin under acid conditions, and contacting a test sample with a reaction system which utilizes at least aconitase, a reducing reagent, citric acid, isocitrate dehydrogenase and (thio)NAD(P). According to the present invention, an accurate and efficient measurement of iron in the serum is possible, even for minute levels of iron. In addition, the present invention assays unsaturated iron binding capacity by adding excess iron to a test sample to bind iron to transferrin, binding the remaining unbound iron to aconitase, and measuring the activated aconitase. According to the present invention, a quick and easy assay of unsaturated iron binding capacity of body fluids, etc. is possible without the need for expert skill.

34 Claims, 4 Drawing Sheets

F I G. 2
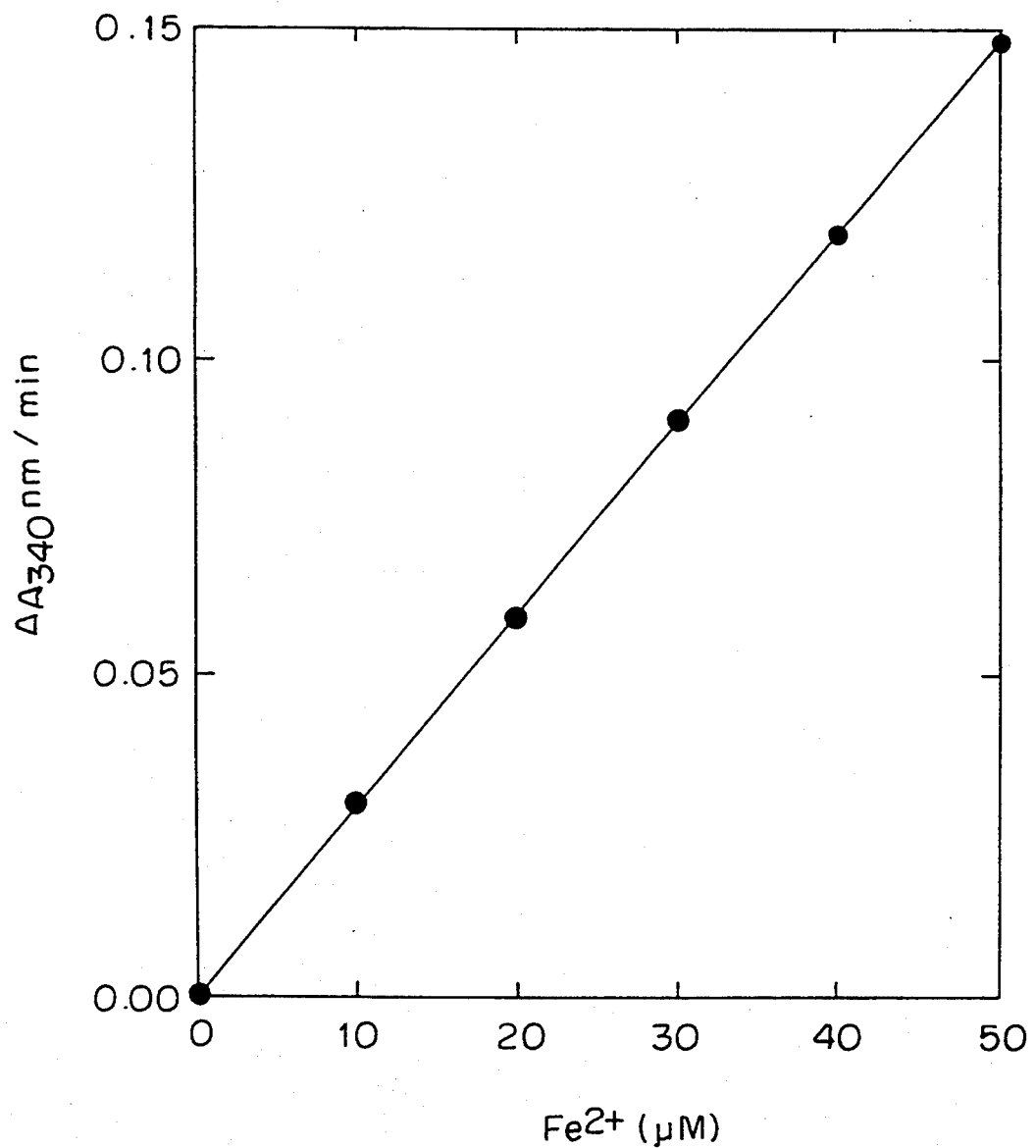

ASSAY METHOD AND ASSAY REAGENT FOR SERUM IRON OR UNSATURATED IRON BINDING CAPACITY

FIELD OF THE INVENTION

The present invention relates to an assay method for serum iron, and more specifically, it relates to a highly-sensitive enzyme assay method in which iron bound to transferrin is liberated, apo-aconitase (EC 4.2.1.3) which exhibits no activity without iron is contacted therewith for activation, and isocitric acid produced from citric acid is subjected to a reaction with isocitrate dehydrogenase (EC 1.1.1.41, EC 1.1.1.42) to make an assay of the serum iron level, and relates to a reagent used for measuring.

The present invention further relates to an enzyme assay method for unsaturated iron binding capacity (hereunder abbreviated to UIBC), and more specifically, to a highly sensitive enzyme assay method for UIBC in which an excess amount of iron of known concentration is added to a subject test sample of body fluid, etc. and the iron is bound to transferrin to saturation, after which the unbound residual iron is contacted with apo-aconitase (EC 4.2.1.3) which exhibits no activity without iron, and isocitric acid produced from citric acid by a catalytic effect of aconitase is measured for its aconitase activity, using isocitrate dehydrogenase (EC 1.1.1.41, EC 1.1.1.42) as the detection enzyme, in order to determine UIBC, and relates to a reagent used for the assay.

PRIOR ART AND PROBLEMS THEREOF

The total amount of iron in the body is about 4 g, two-thirds of which exists in the erythrocyte hemoglobin, and the remaining one-third of which is kept in the tissues of the liver, spleen, bone marrow, etc. as stored iron. The total amount of serum iron is 3–4 mg, and all of it exists bound to transfertin belonging to a serum $\beta$-globulin, (one molecule of transferrin combines with two molecules of iron). The serum iron concentration is regulated by the rate of production and destruction of erythrocytes, and if there is a decline in hematopoiesis in the bone marrow, the flow of serum iron stagnates, raising the serum iron concentration, while the serum iron concentration is lowered in the opposite case. This has led to the conclusion that the serum iron concentration is a reflection of the function of the hematogenous organs. In addition, the dynamics of stored iron also affects serum iron. For example, in diseases such as hepatitis, stored iron in the liver moves to other tissues, causing a rise in serum iron. As described above, serum iron plays a part not only in hemodyscrasia (iron deficiency anemia, aplastic anemia, pernicious anemia, hemolytic anemia, leukemia, polycythemia rubra, etc.), but also in a variety of other diseases (infectious diseases, acute hepatitis, liver cirrhosis, hemochromatosis, nephrosis, etc.), and therefore iron measurement is considered important in clinical examinations.

Assay methods for serum iron include the Matsubara method, the Standard method of International Committee for Standardization in Hematoloby (ICSH), the autoanalyzer method, the atomic absorption spectrophotometry, and so on. The principle of the Matsubara method and the Standard method of International Committee for Standardization in Hematology (ICSH) involve liberation of iron with an acid, deproteinization and reduction of the iron with a reducing reagent, followed by coloring with a color former. However, the molar absorption coefficient of BPT is small and the sensitivity is low, and therefore a large amount of serum is required. Further, as it is also susceptible to interference, it is difficult to deal with many samples simultaneously by to manual treatment. The autoanalyzer method is based on a simple automation of the principle used in the Matsubara method and the Standard method of Internation Committee for Standardization in Hematology (ICSH), without solving the problem of sensitivity, and thus interference by hemoglobin, billrubin, etc. is observed. The atomic absorption spectrophotometry is disadvantageous in that it necessitates pre-treatment and produces large variations in measurement values depending on differences in the procedure used, and the sensitivity is poor. In addition, it also requires special expensive equipment.

PROBLEMS TO BE SOLVED BY THE INVENTION

The present invention aims to overcome all of the disadvantages of the methods of the prior art described above, by providing a novel higly sensitive analysis system for measuring the amount of iron in the body, particularly in the serum, in an accurate, simple and quick manner without the need of expert skill, which allows automation or simultaneous treatment of many samples.

MEANS TO SOLVE THE PROBLEMS

The present invention was developed in order to achieve the object described above, and we the inventors of the present invention conducted a detailed investigation of the relationship between iron and various enzyme activities in order to make a quick and accurate assay of serum iron levels. As a result, we discovered that iron is required for aconitase to express its enzyme activity, which enzyme activity changes in correspondence with the increase in the serum iron level, and confirmed that is is possible to measure the serum iron level by measuring said change, thus completing the present invention.

It is well known that iron is required for aconitase to exert its activity (Proteins, Nucleic Acids and Enzymes, Vol. 22, No. 12, 1293–1302, 1977; THE JOURNAL OF BIOLOGICAL CHEMISTRY Vol. 236, No. 12, 3086–3092 December 1961; THE JOURNAL OF BIOLOGICAL CHEMISTRY, Vol. 242, NO. 8, Issue of April 25, pp. 1870–1979, 1967; THE JOURNAL OF BIOLOGICAL CHEMISTRY, Vol. 246, No. 3, Issue of February 10, pp. 772–779, 1971; Cell, Vol. 64, 881–883, Mar. 8, 1991). However, none of these articles mentions methods for measuring low concentrations of iron such as serum iron (Normal levels in the serum: male=11.6–34.9 $\mu$M, female=7.29–29.5 $\mu$M) or for obtaining such a linear standard curve as normally used in clinical examinations. The method according to the present invention allows a reproducible and highly sensitive measurement of low concentrations of serum iron using a satisfactory linear standard curve.

BRIEF DESCRIPTION OF THE FIGURES

FIG. 2 is an iron measurement curve which was measured according to the method described in Example 4.

Figure 1:
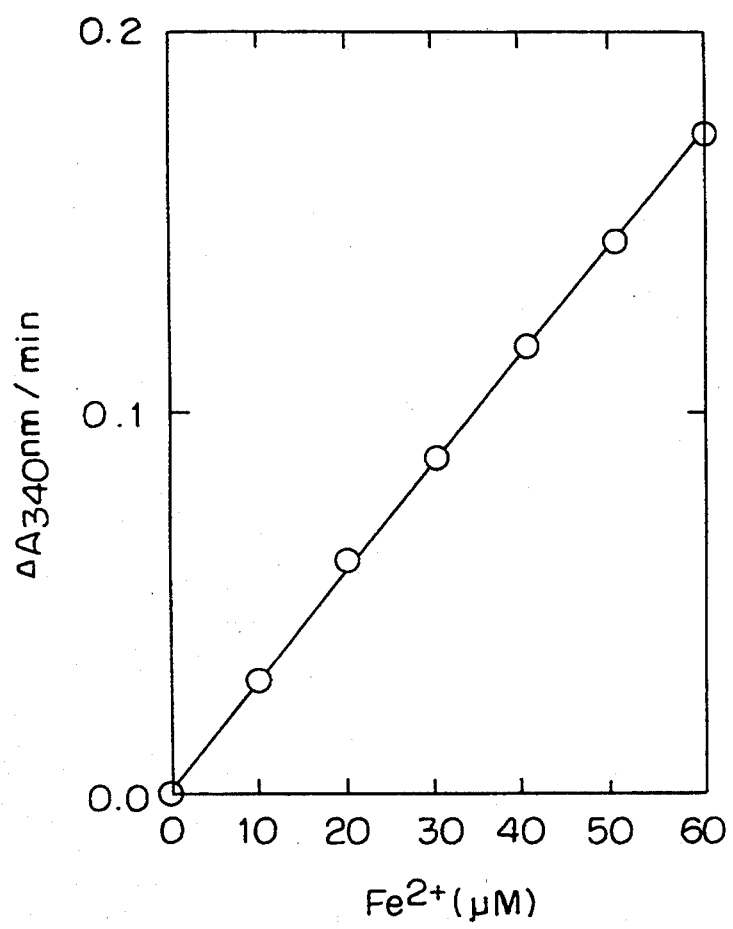
FIG. 1 is an iron measurement curve which was measured according to the method described in Example 1.

The basic principle employed by the present invention involves measurement of a serum iron level in a serum iron assay by liberating the iron bound to transferrin, forming active aconitase, and detecting the aconitase activity which changes in a serum iron concentration-dependent manner, with isocitrate dehydrogenase which acts on isocitric acid produced by a reaction of aconitase, in terms of the degree of conversion of an oxidized nicotinamide adenine dinucleotide class compound (hereunder referred to as NAD class compound) and/or an oxidized nicotinamide adenine dinucleotide phosphate class comound (hereunder referred to as NADP class compound) into a reduced NAD class compound (hereunder referred to as NADH class compound) and/or a reduced NADP class compound (hereunder referred to as NADPH class compound), in order to measure the serum iron level. In concrete terms, iron bound to transferrin is liberated in a solution of an acid pH, and is added to a buffer solution in which at least apo-aconitase has been dissolved, to convert the apo-aconitase into holo-aconitase, and the amount or rate of production of a NADH class compound and/or NADPH class compound is measured with an appropriate buffer solution containing at least citric acid, in order to measure the serum iron level.

In contrast to the Matsubara method, the Standard method of International Committee for Standardization in Hematology (ICSH), the autoanalyzer method and the atomic absorption spectrophotometry which can only obtain one response per iron, the enzymatic assay method according to the present invention can obtain multiple responses per iron due to the effect amplified by the enzyme, and thus provides high sensitivity and precision. It is also superior to presently used methods of measurement from the point of view of its high specificity to iron.

All iron in the serum is bound to transferrin. According to the present invention, iron is measured by measuring aconitase activity either after the iron is liberated from transferrin in the serum and bound to aconitase, or while allowing the iron which is liberated from transfertin in the serum to bind to aconitase.

As a result of multi-faceted research to find a method to liberate iron from transferrin in the serum in a quantitative manner, having absolutely no adverse effect on the measurement of iron conducted thereafter and easy to handle, we discovered that the desired object can be achieved in an acid environment. Therefore, in the present invention, an acid pH range is maintained for the step of liberation, and any method may be used to that aim, including, for example, utilizing an acid buffer solution.

The buffers used in the step of liberation of the serum iron bound to transferrin include an acetate buffer, a GTA buffer, an oxalic acid buffer, a phosphate buffer, a glycine buffer, an HCl-KCl buffer, a potassium biphtalate buffer, a succinate buffer, etc., but there are no particular restrictions so long as the optimum pH of the buffer solution is in the range of 1–5, preferably 2–4, and the concentration of the reagent used is 1–1,000 mM, preferably 10–500 mM. Also, a surfactant, reducing etc. may be added thereto to increase the effectiveness.

Examples of surfactants include anionic surfactants, cationic surfactants, ampholytic surfactants, nonionic surfactants, steroid skeleton-containing surfactants, etc.

The reducing reagents which may be used according to the present invention include ascorbic acid, thioglycolic acid, thiomalate, cysteine, N-acetylcysteine, hydroxylamine, 2-mercaptoethanol, reduced glutathione, dithiothreitol, dithioerythritol, 2-aminoethylisothiouronium bromide and thioglycerol, etc., as well as any reducing reagents which promote the binding of iron to aconitase. The reagent concentration is 0–1,000 mM, preferably 0.1–500 mM.

There are no particular restrictions on the aconitase used according to the present invention, so long as its activity varies depending on the addition or non-addition of iron. Also, treatment with a chelating reagent may be employed to adjust apo-aconitase. Effective chelating reagents include ethylenediamine tetraacetatic acids (EDTA), hydroxyethylethylenediamine triacetic acid (EDTA-OH), cyclohexanediamine tetraacetic acid (CyDTA), diethylenetriamine pentaacetic acid (DTPA), glycol ether diamine tetraacetic acid (GEDTA), triethylenetetraamine hexaacetic acid (TTHA), diaminopropanol tetraacetic acid (DPTA-OH), o-phenanthroline, etc., but it is preferable to have as small a background as possible with no iron added thereto. Further, the ethylenediamine tetraacetic acids (EDTA) may be an alcohol precipitate or crystals of a free acid or a salt with an alkali such as, sodium, ammonium, etc., and is not particularly limited. The enzyme is added at a concentration of 0.01–100 u/ml, preferably 0.1–30 u/ml.

The isocitrate dehydrogenase which may be used according to the present invention is preferably one with a low Km value with respect to isocitric acid, but it is not particularly limited as long as it is capable of reacting with the isocitric acid produced by the reaction. It may be either specific to an NAD class compound or specific to an NADP class compound. The concentration of the enzyme added is 0.01–200 u/ml, preferably 0.1–20 u/ml. Also, magnesium ions or manganese ions are necessary for the exertion of the enzyme activity of isocitrate dehydrogenase and aconitase, and the concentration of such a reagent is 0.5 $\mu$M–100 mM, preferably 5 $\mu$M–10 mM.

The NAD and/or NADP class compounds used according to the present invention may be an alcohol precipitate or crystals of a free acid or a salt with an alkaline metal, ammonium, etc., and should be of high purity, but normal commercially available NAD and NADP class compounds are adequate for use according to the present invention. The NAD and NADP class compounds available for use as coenzymes for isocitrate dehydrogenase in the method according to the present invention include, of course, NAD and NADP, as well as thio-NAD and thio-NADP. Other NAD and NADP class compounds, e.g., acetyl-NAD, deamino-NAD, acetyl-NAPD, leamino-NAPD, etc., which can react with isocitrate dehydrogenase may be employed in the method according to the present invention. The concentration of such reagents is 0.01–100 mM, preferably 0.1–10 mM.

The buffer solution for use in the step of binding of iron to aconitase and in the step of measurement of aconitase activity is not particularly limited, and examples include a PIPES buffer, a Tris buffer, a Triethanolamine buffer, a glycine buffer, a GTA buffer, a phosphate buffer, a borate buffer, etc. The optimum pH of the buffer solution is in the range of 5-9, preferably 6-8, while the concentration of the reagent is 1-1,000 mM, preferably 10-500 mM.

The composition for the serum iron measurement according to the present invention comprises a first reagent at pH 1-5, and preferably at pH 2-4, a second reagent containing at least 0.01-300 u/ml, preferably 0.1-30 u/ml of aconitase, and a third reagent containing at least 0.01-1,000 mM, preferably 0.1-100 mM of citric acid. A reducing reagent, isocitrate dehydrogenase, an NAP and/or NADP class compound, magnesium ions or manganese ions are added to one or more of the three reagents. It is recommended to add a reducing reagent to the first and second reagents, and isocitrate dehydrogenase, an NAD and/or NADP class compound, magnesium ions or manganese ions to the third reagent.

Further, the composition for measurement of serum iron according to the present invention by measuring aconitase activity while allowing the iron which is liberated from transferrin in the serum to bind to aconitase, comprises a first reagent at pH 1-5, preferably at pH 2-4, a second reagent containing at least 0.01-300 u/ml, preferably 0.1-30 u/ml of aconitase and 0.01-200 u/ml, preferably 0.1-20 u/ml of isocitrate dehydrogenase. A reducing reagent, an NAD and/or NADP class compound, magnesium ions or manganese ions are added to either or both of the reagents.

An explanation will now be given regarding the enzymatic assay method for unsaturated iron binding capacity according to the present invention.

Normally, all serum iron in the blood is bound to transferrin, and in healthy individuals, about one-third of the transferrin is saturated with iron, while the remaining two-thirds is in an unsaturated state, unbound to iron. UIBC refers to the amount of unsaturated transferrin which is not bound to iron, and is expressed in terms of the amount of binding iron. As is well known, the sum of serum iron and UIBC is called the total iron binding capacity (sometimes referred to hereafter as "TIBC"). It was mentioned previously that the measurement of serum iron is important in clinical examinations, but when combined with a measurement of UIBC, it is possible to obtain a more detailed understanding of the condition of the disease. UIBC measurement is particularly effective in the diagnosis of iron deficiency anemia, where confirmation is made of the decrease in serum iron level and the increase in UIBC-/TIBC. Since other diseases such as chronic infection and malignant tumors which cause a decrease in serum iron also cause a decrease in UIBC/TIBC, they may thus be easily distinguished from iron deficiency anemia. In aplastic anemia, an increase in serum iron and a decrease in UIBC/TIBC are observed. Measurement of only UIBC is of great significance in clinical examinations, but measurement of both serum iron and UIBC or serum iron and TIBC provides more detailed information and thus has greater significance.

In order to satisfactorily carry out the method according to the present invention, it is necessary first to prepare (1) a stable, alkaline, excess iron solution of known concentration in order to fully saturate the transferrin with iron; (2) an iron solution which completely saturates the transferrin with iron shortly after mixing the body fluid with the iron solution, in order to be ready to the autoanalysis; and (3) an iron solution which does not cause non-specific adsorption of the iron therein to substances other than transferrin.

Of the above points, (1) is the most difficult, since the intrinsic properties of iron ion are such that the ion can stably exist under acid pH conditions, such as in an aqueous solution of nitric acid, hydrochloric acid, etc., but in slightly acid to alkaline conditions forms iron hydroxide, causing sedimentation or adsorption onto the appliances and therefore iron cannot exist stably at a pH which is favorable for the binding of iron to transferrin, for example, a pH of 7-10, and preferably 8-9. However, usually a somewhat stable bivalent iron compound (ammonium iron (II) sulfate or ferrous chloride), rather than a trivalent iron compound, is used in a Tris hydroxylmethylaminomethane (hereunder abbreviated to "Tris") buffer solution in the co-presence of a reducing reagent such as ascorbic acid, etc., for stabilization. If this is still inadequate, nitrilo triacetate may be added, and the method of further improving stability (Japanese Patent Application JP-B SHO 52-9160) may be adapted to the method according to the present invention. Also, as described in Japanese Patent Application JP-A HEI 2-167476, though with a different purpose, it is effective to add a chelating reagent, for example, ethylenediamine-N,N'-diacetic acid, hydroxyethyliminodiacetic acid, nitrilotriacetic acid, etc. In Japanese Patent Application JP-A HEI 2-167476, addition of these chelating reagents allows transferrin to be completely saturated with iron shortly after mixing a sample to be tested and the iron solution together, thus also satisfying point (2) above.

Another method for satisfying point (2) which may be effectively employed in the method according to the present invention is a method wherein a hydroxyacid such as a glycolic acid, lactic acid, α-oxybutyric acid, glyceric acid, tartronic acid, malic acid, tartaric acid, citric acid or mandelic acid is used as the buffer instead of Tris, for a more rapid saturation of transferrin than with Tris (Japanese Patent Application JP-A SHO 60-69557). Also, point (3) is essentially to prevent non-specific adsorption to albumin in particular, and a method is known which avoids this by the addition of, for example, a surfactant (Japanese Patent Application JP-A HEI 2-156160).

The addition of a sufactant as described in Japanese Patent Application JP-A HEI 2-156160 has been confirmed to be effective in the method according to the present invention. The pH of the Tris or hydroxyacid buffer solution should be about 7-10, preferably 8-9, the concentration used should be about 1-1,000 mM, preferably 10-500 mM, and the concentration of the chelating reagent should be such that it does not inhibit the binding of iron to transferrin, and does not stop the binding of the residual iron to aconitase. The optimum concentration differs depending on the chelating reagent used, but is normally 0.01-100 mM, preferably 0.1-10 mM. The optimum concentration of the surfactant also differs depending on the type used, but non-specific adsorption is considerably suppressed by the addition thereof at a concentration of 0.001-10%, preferably 0.01-5%.

The binding of iron to aconitase requires the presence of a reducing reagent. It is easy to cause binding of the iron to aconitase by the reductivity of a certain reducing reagent which is added to the iron solution for the stabilization of said iron, but there is no problem with further adding the reducing reagents to the aconitase solution. Effective reducing reagents available for use include ascorbic acid, thioglycolic acid, thiomalate, cysteine, N-acetylcysteine, hydroxylamine, 2-mercaptoethanol, reduced glutathione, dithiothreitol, dithioerythritol, 2-aminoethylisothiouronium bromide and thioglycerol, etc., as well as any reducing reagent which promotes the binding of iron to aconitase. The reagent concentration is up to 1,000 mM, preferably 0.1–500 mM.

There are no particular restrictions on the aconitase used according to the present invention, so long as its activity varies depending on the addition or non-addition of iron. Also, treatment with a chelating reagent may be employed to adjust apoaconitase. Effective chelating reagents include ethylenediaminetetraacetic acid, hydroxyethylethylenediaminetriacetic acid, cyclohexanediaminetetraacetic acid, diethylenetriaminepentaacetic acid, glycoletherdiaminetetraacetic acid, triethylenetetraaminehexaacetic acid, diaminopropanoltetraacetic acid, o-phenanthroline, etc., but it is preferable to have as small a background as possible with no iron added thereto. Further, the ethylenediaminetetraacetic acid may be an alcohol precipitate or crystals of a free acid or a salt with an alkaline metal, ammonium, etc., and is not particularly limited. In cases where the background cannot be made small even by treatment with a chelating reagent, it may be re-purified with CM-Sepharose, etc. The enzyme is added at a concentration of 0.01–100 u/ml, preferably 0.1–30 u/ml.

The isocitrate dehydrogenase used to detect aconitase activity is preferably one with a low Km value with respect to isocitric acid, but it is not particularly limited as long as it is capable of reacting with the isocitric acid produced by the reaction. It may be either specific to NAD class compounds or specific to NADP class compounds. The concentration of the enzyme added is 0.01–200 u/ml, preferably 0.1–20 u/ml. Also, magnesium ions or manganese ions are necessary for the exertion of the enzyme activity of isocitrate dehydrogenase and aconitase, and the concentration of such a reagent is 0.5 $\mu$M–100 mM, preferably 5 $\mu$M–10 mM.

The NAD and/or NADP class compounds used may be an alcohol precipitate or crystals of a free acid or a salt with an alkaline metal, ammonium, etc., and are preferable to be of high purity, but normal commercially available NAD and NADP class compounds are adequate for use according to the present invention. NAD and NADP class compounds available for use in the method according to the present invention include, of course, NAD and NADP as well as thio-NAD and thio-NADP. Other NAD and NADP class compounds which can react with isocitrate dehydrogenase may be employed in the method according to the present invention. The concentration of such reagents is 0.01–100 mM, preferably 0.1–10 mM.

The composition for use in the UIBC measurement according to the present invention comprises a first reagent at pH 7–10, and preferably at pH 8–9 which contains at least iron, a second reagent containing at least 0.01–300 u/ml, preferably 0.1–30 u/ml of aconitase, and a third reagent containing at least 0.01–1,000 mM, preferably 0.1–100 mM of citric acid. A reducing reagent, isocitrate dehydrogenase, an NAD and/or NADP class compound, magnesium ions or manganese ions are added to one or more of the three reagents. It is recommended to add a reducing reagent to the first and second reagents, and isocitrate dehydrogenase, an NAD and/or NADP class compound, magnesium ions or manganese ions to the third reagent. The present invention is, as described above, an assay method for UIBC characterized by using enzyme in the reaction system. The present invention also relates to a reagent and a measuring kit.

Examples according to the present invention are given below.

EXAMPLE 1

Reagents R-1 and R-2 were prepared having the compositions listed below in Table 1.

TABLE 1

| | Reagent R-1: |
|---|---|
| 50 mM | Sodium acetate, pH 3.0 |
| 50 mM | Ascorbic acid |
| 2 mM | Sodium citrate |
| | Reagent R-2: |
| 100 mM | PIPES buffer, pH 7.4 |
| 1.5 u/ml | Aconitase |
| 2.5 u/ml | Isocitrate dehydrogenase |
| 0.6 mM | NADP+ |
| 0.6 mM | Magnesium sulfate |

Assay method

The standard iron solution used was a 0–60 $\mu$M ammonium iron (II) sulfate solution. Sixty $\mu$l of reagent R-1 was added to 20 $\mu$l of the sample (serum sample and standard iron solution) and the mixture was stirred and incubated at 37° C. for 5 minutes, after which 200 $\mu$l of reagent R-2 was added thereto, and stirred at the same temperature and allowed to stand for 4 minutes, after which the degree of absorbance variation during 1 minute was measured with a Hitachi 7150-model autoanalyzer. The degree of absorbance variation of 0 $\mu$M of the ammonium iron (II) sulfate solution was subtracted therefrom and a graph was drawn. The results are shown in FIG. 1. As will be understood from FIG. 1, when the method according to the present invention is used, a favorable linearity from the starting point was obtained.

EXAMPLE 2

Reagents R-1 and R-2 are identical to those in Table 1 of Example 1.

Assay method

The assay method is the same as in Example 1, and was used to measure serum samples. The number of "n" was 10. Also, the variation coefficients of the serum samples are shown in Table 2. The CV values of the serum samples were favorable values of under 3%, as shown in Table 2.

TABLE 2

| | Serum iron level ($\mu$M) | |
|---|---|---|
| | Sample 1 | Sample 2 |
| 1 | 14.30 | 32.54 |
| 2 | 14.89 | 32.64 |
| 3 | 15.04 | 32.35 |
| 4 | 14.91 | 32.10 |
| 5 | 14.72 | 32.51 |
| 6 | 14.09 | 33.32 |
| 7 | 14.76 | 31.95 |
| 8 | 14.81 | 31.40 |
| 9 | 14.33 | 32.34 |
| 10 | 14.01 | 31.90 |
| Average | 14.59 | 32.31 |
| S.D. | 0.35 | 0.49 |
| C.V (%) | 2.40 | 1.52 |

EXAMPLE 3

The measurement of serum iron of samples was made using both the present method of measurement and a kit manufactured by Wako Junyaku (Nitroso-PSAP direct method Fe-TR).

Reagents R-1 and R-2 used in the present method of measurement were the same as those used in Example 1 (Table 1).

Measuring method

The same measuring method as in Example 1 was used to measure serum samples. The number of samples was 10. As can be seen from the results in Table 3, it is possible to make an accurate measurement of serum iron with the present invention.

TABLE 3

| | Serum iron level ($\mu$M) | |
|---|---|---|
| Serum sample | Present measuring method | Fe-TR method |
| 1 | 5.38 | 5.24 |
| 2 | 7.28 | 7.36 |
| 3 | 15.29 | 14.86 |
| 4 | 19.37 | 20.14 |
| 5 | 24.79 | 24.45 |
| 6 | 32.37 | 32.56 |
| 7 | 36.17 | 36.73 |
| 8 | 42.35 | 41.28 |
| 9 | 46.35 | 46.50 |
| 10 | 53.94 | 54.18 |

EXAMPLE 4

Reagents R-1, R-2 and R-3 were prepared having the compositions listed below in Table 4.

TABLE 4

| | | |
|---|---|---|
| | Reagent R-1: | |
| 200 mM | | Sodium acetate, pH 3.0 |
| 200 mM | | Ascorbic acid |
| | Reagent R-2: | |
| 150 mM | | PIPES buffer, pH 6.3 |
| 50 mM | | Ascorbic acid |
| 1 u/ml | | Aconitase |
| | Reagent R-3: | |
| 100 mM | | PIPES buffer, pH 7.4 |
| 1 mM | | Sodium citrate |
| 4 u/ml | | Isocitrate dehydrogenase |
| 1 mM | | NADP$^+$ |
| 1 mM | | Magnesium sulfate |

Assay method

The standard iron solution used was a 0-50 $\mu$M ammonium iron (II) sulfate solution. An equal amount of reagent R-1 was added to a serum sample and the standard iron solution, and the mixture was stirred and placed in a sample cup. To 20 $\mu$l of the mixture was added 100 $\mu$l of reagent R-2, and the resulting mixture was stirred and incubated at 37° C. for 5 minutes, followed by the addition of 90 $\mu$l of reagent R-3. Next, the thus-obtained mixture was further stirred at the same temperature and allowed to stand for 2 minutes. Then, the degree of absorbance variation during 1 minute was measured with a Hitachi 7150-model autoanalyzer. The "n" number was 15. The degree of absorbance variation of a 0 $\mu$M ammonium ferrous sulfate solution was subtracted therefrom and a graph was drawn.

The results are shown in FIG. 2. As will be understood by referring to FIG. 2, when the method according to the present invention is used, a favorable linearity from the starting point was obtained. Also, the variation coefficients of the serum samples and the standard iron solution are shown in Table 5. The CV values of the serum samples and the standard iron solution were favorable values of under 3%, as shown in Table 5.

TABLE 5

| | cv (%) |
|---|---|
| Standard iron solution | |
| 10 $\mu$M | 2.28 |
| 20 $\mu$M | 1.29 |
| 30 $\mu$M | 1.85 |
| 40 $\mu$M | 1.79 |
| 50 $\mu$M | 1.24 |
| Serum sample | |
| Sample 1 (18 $\mu$M) | 1.17 |
| Sample 2 (34 $\mu$M) | 1.27 |

EXAMPLE 5

Each of the reagents was prepared having the compositions listed below in Table 6, and measurement was made using an autoanalyzer, according to the procedure described below.

TABLE 6

| | | |
|---|---|---|
| Reagent-1'b: | 160 mM | Tris-HCl buffer solution, pH 9 |
| Reagent-1's: | 160 mM | Tris-HCl buffer solution, pH 9 |
| | 19 $\mu$M | Ammonium iron (II) sulfate |
| Reagent-2: | 150 mM | PIPES-NaOH, pH 6.5 |
| | 50 mM | Ascorbic acid |
| | 1 u/ml | Aconitase |
| Reagent-3: (NAD system) | 100 mM | PIPES-NaOH, pH 7.7 |
| | 1 mM | Sodium citrate |
| | 1 mM | NAD |
| | 1 mM | Magnesium sulfate |
| | 0.5 mM | AMP |
| | 4 u/ml | Isocitrate dehydrogenase (NAD) |
| Reagent-3: (NADP system) | 100 mM | PIPES-NaOH, pH 7.7 |
| | 1 mM | Sodium citrate |
| | 1 mM | NADP |
| | 1 mM | Magnesium sulfate |
| | 4 u/ml | Isocitrate dehydrogenase (NAD) |

Procedure

Reagent-1'b and Reagent-1's were mixed together at ratios of 5:0, 4:1, 3:2, 2:3, 1:4 and 0:5, and purified water was added thereto at a proportion of 1:1/10 (mixture:-water) to prepare samples for the autoanalyzer (Hitachi 7150). Seven $\mu$l of each sample was added to Reagent-2 (100 $\mu$l), and incubation was effected at 37° C. for 5 minutes. Reagent-3 (NAD or NADP system, 90 $\mu$l) was then added thereto, and incubation was effected at the same temperature for 2 minutes, and the increase rate of the absorbance at 340 nm during 1 minute was measured. The absorbance variation with reagent-1'b and reagent-1's at a ratio of 5:0 was defined as the blank value, and the difference between the measurements of each sample and the blank value was plotted. The results are shown in FIG. 3.

Figure 3:
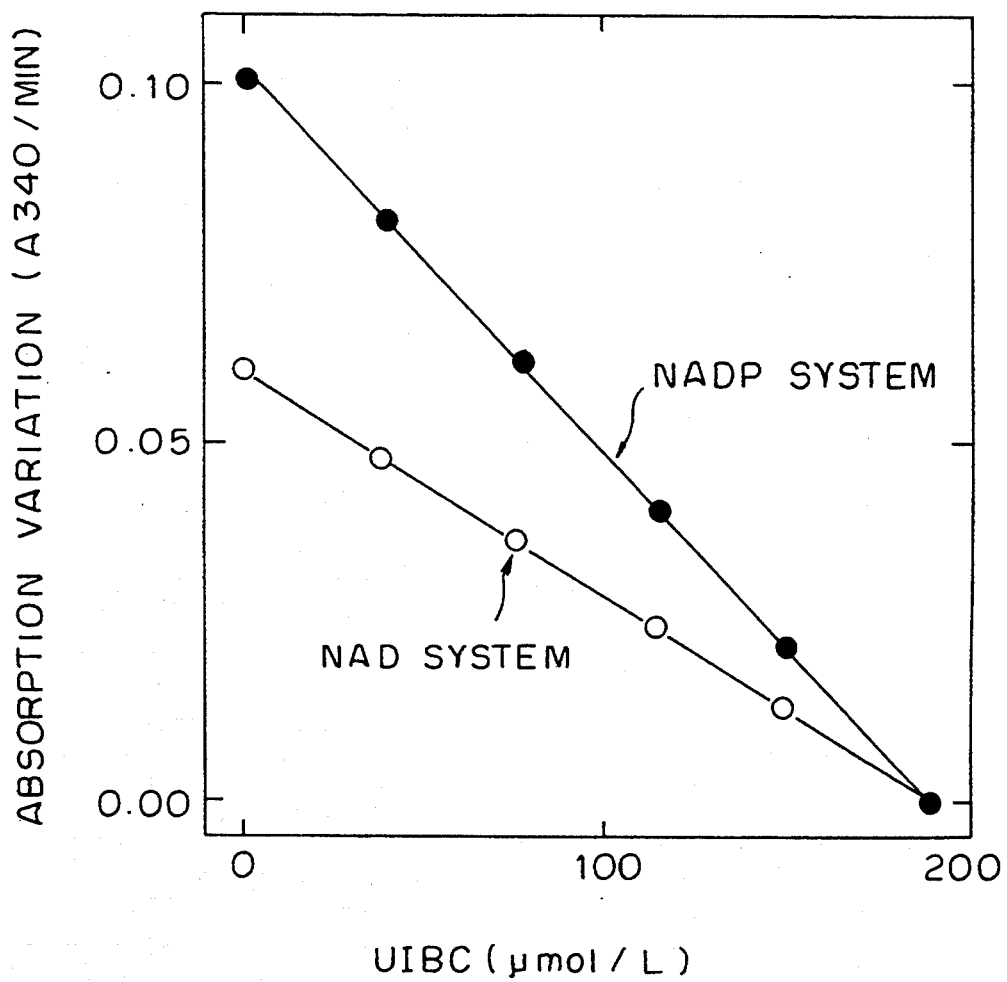
FIG. 3 is a UIBC measurement curve which was measured according to the method described in Example 5.

As shown in FIG. 3, in the method according to the present invention, a favorable linearity was exhibited for a UIBC value of 0-190 $\mu$M.

EXAMPLE 6

Each of the reagents were prepared having the compositions listed below in Table 7, and measurement was made using an autoanalyzer, according to the procedure described below.

TABLE 7

| | | |
|---|---|---|
| Reagent-1b: | 160 mM | Tris-HCl buffer solution, pH 9 |
| | 0.1% | N-lauroylsarcosinate |
| | 0.1 mM | Hydroxyethyliminodiacetic acid |
| Reagent-1s: | 160 mM | Tris-HCl buffer solution, pH 9 |

TABLE 7-continued

|  | 0.1% | N-lauroyl sarcosinate |
|---|---|---|
|  | 0.1 mM | Hydroxyethyliminodiacetic acid |
|  | 50 μM | Ammonium iron (II) sulfate |
| Reagent-2: | 150 mM | PIPES-NaOH, pH 6.5 |
|  | 50 mM | Ascorbic acid |
|  | 0.5 u/ml | Aconitase |
| Reagent-3: (NADP system) | 100 mM | PIPES-NaOH, pH 7.7 |
|  | 1 mM | Sodium citrate |
|  | 1 mM | NADP |
|  | 1 mM | Magnesium sulfate |
|  | 4 u/ml | Isocitrate dehydrogenase |

Procedure

Figure 4:
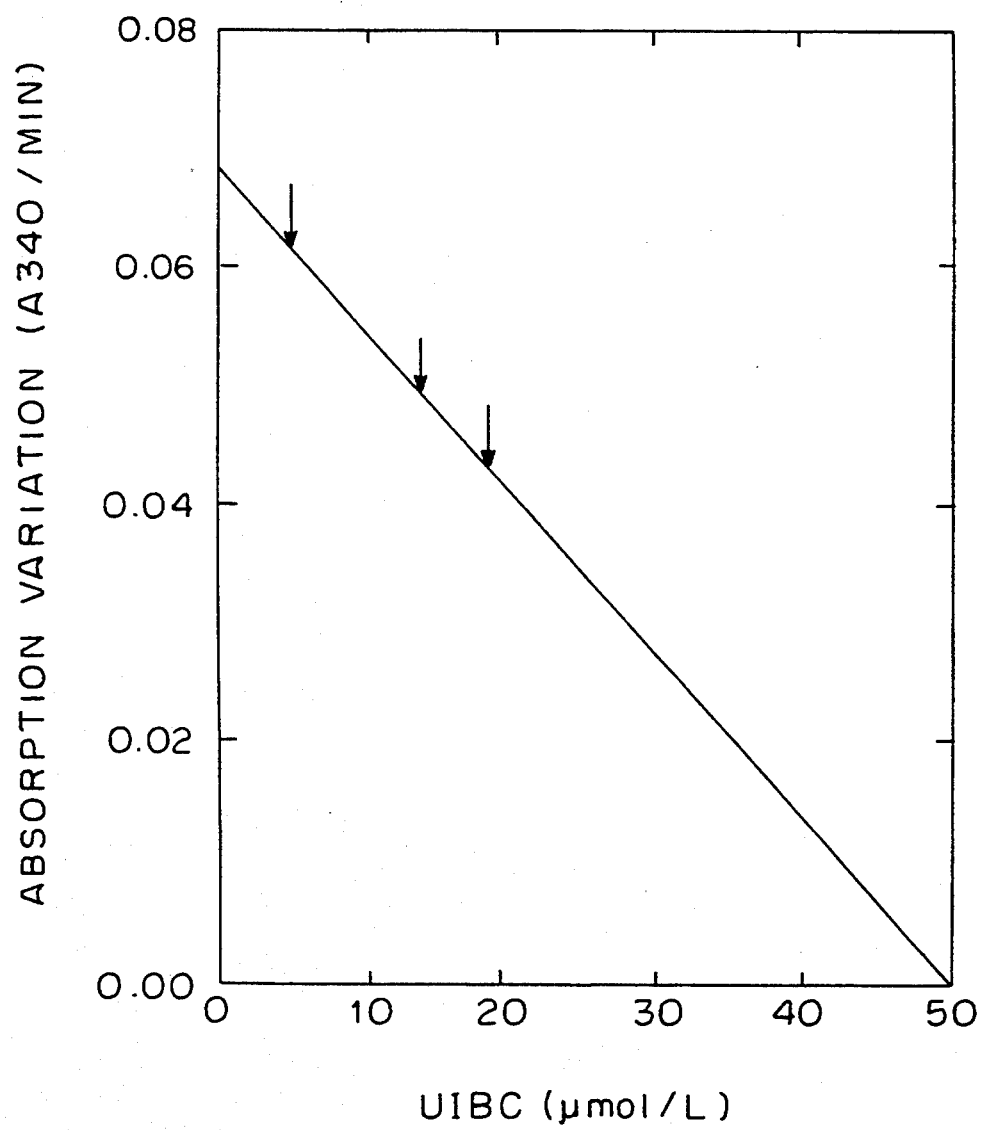
FIG. 4 shows a UIBC measurement curve which was measured according to the method described in Example 6, and the serum UIBC values obtained thereby.

Reagent-1b and reagent-1s were mixed with equal volume of 3 types of serum, and the mixture was used as the test sample for the autoanalyzer (Hitachi 7150). Also, reagent-1b and reagent-1s were mixed with equal volume of 0.9% NaCl to prepare a blank test sample and a standard sample for the autoanalyzer (Hitachi 7150). Five μl of the sample was added to reagent-2 (100 μl), and incubation was effected at 37° C. for 5 minutes. Reagent-3 (90 μl) was then added thereto, and incubation was further effected at the same temperature for 2 minutes, and the rate of increase in absorbance at 340 nm during 1 minute thereafter was measured. The rate of increase in absorbance obtained from the mixture of reagent-1b with an equal volume of 0.9% NaCl was defined as the blank value, and the standard curve was drawn by the UIBC calculated by subtracting the blank value from the rate of increase in absorbance obtained from the mixture of 0.9% NaCl and an equal volume of reagent-1s. For the test samples, the rate of increase in absorbance obtained by addition of reagent-1b to the serum was subtracted, as the blank value, from the rate of increase in absorbance obtained by addition of reagent-1s to the serum, and reference was made to the standard curve. The results are shown in FIG. 4. In this figure, serum locations are indicated by arrows.

As shown in FIG. 4, three types of serum UIBC were determined using the method according to the present invention, and these were found to be 4.5 μM, 13.4 μM and 18.3 μM, respectively.

We claim:

1. A method for measuring the amount of iron in a fluid sample comprising liberating iron in said fluid sample, adding to the sample an effective amount of aconitase for binding the liberated iron to the aconitase, and measuring resulting aconitase activity.

2. A method for measuring the amount of iron in a serum sample comprising liberating iron in said serum sample, adding to the sample an effective amount of aconitase for binding the liberated iron to the aconitase, and measuring resulting aconitase activity.

3. An enzymatic assay method for serum iron, characterized by including a step of liberation of iron from transferrin in serum, a step of binding the liberated iron to aconitase, and a step of measuring aconitase activity.

4. An enzymatic assay method for serum iron, characterized by including a step of liberation of iron from transferrin, to which iron is bound in blood, and a step of measuring aconitase activity while binding the liberated iron to aconitase.

5. An enzymatic assay method for serum iron according to claim 3, characterized by liberating iron from transferrin, to which iron is bound in serum, at an acid pH.

6. An enzymatic assay method for serum iron which is liberated from transferrin according to claim 3, characterized by using a reducing reagent to bind the iron liberated from transferrin, to which iron is bound in serum, to aconitase.

7. An enzymatic assay method for serum iron according to claim 6, characterized in that the reducing reagent is selected from the group consisting of ascorbic acid, thioglycolic acid, thiomalate, cysteine, N-acetylcysteine, hydroxylamine, 2-mercaptoethanol, reduced glutathione, dithiothreitol, dithioerythritol, 2-aminoethylisothiouronium bromide and thioglycerol.

8. An enzymatic assay method for serum iron according to claim 3, characterized by measuring serum iron level by detecting aconitase activity using isocitrate dehydrogenase to measure rate of production of a compound formed as a result of the aconitase activity.

9. An enzymatic assay method for serum iron according to claim 8, characterized by using a nicotinamide adenine dinucleotide class compound and/or a nicotinamide adenine dinucleotide phosphate class compound as a coenzyme for isocitrate dehydrogenase.

10. A reagent for enzymatic measurement of serum iron consisting essentially of apo-aconitase, a reducing agent, citric acid, isocitrate dehydrogenase, and a compound selected from the group consisting of nicotinamide adenine dinucleotides and nicotinamide adenine dinucleotide phosphates.

11. A reagent for enzymatic measurement of serum iron according to claim 10 wherein the reagent has an acid pH.

12. A reagent for enzymatic measurement of serum iron according to claim 11 wherein the pH of the reagent ranges from 1 to 5.

13. A reagent according to claim 12 wherein the pH of the reagent ranges from 2 to 4.

14. A reagent for enzymatic measurement of serum iron according to claim 10 wherein the reducing agent is selected from the group consisting of ascorbic acid, thioglycolic acid, thiomalate, cysteine, N-acetylcysteine, hydroxylamine, 2-mercaptoethanol, reduced glutathione, dithiothreitol, 2-aminoethylisothiouronium bromide and thioglycerol.

15. A reagent according to claim 10 wherein the reducing agent is present at a concentration of up to 1000 mM.

16. A reagent according to claim 15 wherein the reducing agent is present at a concentration of 0.1–500 mM.

17. A reagent according to claim 10 wherein the apo-aconitase is present in an amount 0.01–300 u/ml.

18. A reagent according to claim 17 wherein the apo-aconitase is present in an amount of 0.01–30 u/ml.

19. A reagent according to claim 10 wherein the isocitrate dehydrogenase is present at a concentration of 0.01–200 u/ml.

20. A reagent according to claim 10 wherein the isocitrate dehydrogenase is present at a concentration of 0.01–20 u/ml.

21. A reagent according to claim 10 wherein the compound selected from the group consisting of nicotinamide adenine dinucleotides and nicotinamide adenine dinucleotide phosphates is present in a concentration of from 0.01 to 100 mM.

22. A reagent according to claim 21 wherein the compound selected from the group consisting of nicotinamide adenine dinucleotides and nicotinamide adenine dinucleotide phosphates is present in a concentration of from 0.1 to 10 mM.

23. A reagent for enzymatic measurement of iron comprising:
- a first reagent composition comprising a buffer at pH 1-4;
- a second reagent composition comprising at least 0.01-300 u/ml apo-aconitase; and
- a third reagent composition comprising at least 0.01-1000 mM citric acid.

24. A reagent according to claim 23 wherein said first reagent composition comprising a buffer is at pH 2-4;
said second reagent composition comprises 0.1-30 u/ml apo-aconitase; and
said third reagent composition comprises 0.1-100 mM citric acid.

25. A method for assaying unsaturated iron binding capacity in a sample comprising:
- adding a known amount of excess iron to said sample to cause binding of iron to transferrin in said sample;
- liberating iron from transferrin in the sample;
- adding an effective amount of aconitase to the sample; and
- measuring aconitase activity.

26. The method according to claim 25 wherein a chelating agent is added during the step of binding iron to transferrin.

27. The method according to claim 25 wherein a surfactant is added during the step of binding iron to transferrin.

28. A method according to claim 25 further comprising adding isocitrate dehydrogenase to the sample and measuring the unsaturated iron binding capacity by detecting aconitase activity.

29. A method according to claim 28 wherein a compound selected from the group consisting of nicotinamide adenine nucleotides and nicotinamide adenine nucleotide phosphates, and mixtures thereof, is used as a coenzyme for isocitrate dehydrogenase.

30. A method for assaying unsaturated iron binding capacity in a sample comprising:
- adding a known quantity of excess iron to said sample to bind iron to transferrin in said sample;
- adding an effective amount of aconitase to the sample;
- binding any remaining unbound iron to aconitase; and
- measuring aconitase activity.

31. A method according to claim 30 wherein a chelating agent is added during the step of binding iron to transferrin.

32. A method according to claim 30 wherein a surfactant is added during the step of binding iron to transferrin.

33. A method according to claim 30 further comprising adding isocitrate dehydrogenase to the sample and measuring the unsaturated iron binding capacity by detecting aconitase activity.

34. A method according to claim 30 wherein a compound selected from the group consisting of nicotinamide adenine nucleotides and nicotinamide adenine nucleotide phosphates, and mixtures thereof, is used as a coenzyme for isocitrate dehydrogenase.

* * * * *